(12) United States Patent
Kumar et al.

(10) Patent No.: US 6,664,058 B2
(45) Date of Patent: Dec. 16, 2003

(54) BASE ANALOGUES

(75) Inventors: Shiv Kumar, Belle Mead, NJ (US); Satyam Nampalli, Belle Mead, NJ (US); Constantin Neagu, West Windsor, NJ (US); Mark McDougall, Arroyo Grande, CA (US); David Loakes, Cambridge (GB); Dan Brown, Cambridge (GB)

(73) Assignees: Amersham Biosciences UK Limited, Buckinghamshire (GB); Medical Research Council Laboratories of Molecular Biology, Cambridge (GB)

( * ) Notice: Subject to any disclaimer, the term of this patent is extended or adjusted under 35 U.S.C. 154(b) by 0 days.

(21) Appl. No.: 09/898,210

(22) Filed: Jul. 3, 2001

(65) Prior Publication Data
US 2002/0137695 A1 Sep. 26, 2002

(30) Foreign Application Priority Data
Jul. 3, 2000 (GB) .............................................. 0016258

(51) Int. Cl.[7] .............................. C12Q 1/68; C12P 19/34; C07H 21/02; C07H 21/00
(52) U.S. Cl. ........................ 435/6; 435/91.1; 435/91.2; 536/23.1; 536/25.3
(58) Field of Search .......................... 435/6, 91.1, 91.2; 536/23.1, 25.3

*Primary Examiner*—Kenneth R. Horlick
*Assistant Examiner*—Young Kim
(74) *Attorney, Agent, or Firm*—Royal N. Ronning, Jr.; Stephen G. Ryan

(57) ABSTRACT

The present invention describes novel compounds of the formula

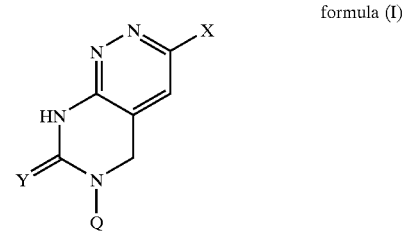

formula (I)

Wherein Q is H or a sugar or a sugar analogue or a nucleic acid backbone or backbone analogue, Y=O, S, NR[10], where R[10] is H, alkyl alkenyl, alkynyl, X is H, alkyl, alkenyl, alkynyl, aryl, heteroaryl or a combination thereof or, preferably, a reporter group. The novel compounds are suitable for incorporation in oligonucleotides and polynucleotides.

12 Claims, No Drawings

BASE ANALOGUES

INTRODUCTION

The present invention relates to novel compounds e.g. modified base analogues that can be used to label nucleic acids which can be used in a wide variety of molecular biology applications.

BACKGROUND

Nucleic acid molecules labelled with reporter groups have been used in many molecular biology techniques such as sequencing and hybridisation studies. The labelled nucleic acid molecules have been produced by a variety of methods. These methods have included labelled nucleoside, deoxynucleoside, or dideoxynucleoside triphosphates, labelled phosphoramidites and direct coupling of labels to nucleic acids (Renz, EP 120376). The labelled nucleotides and labelled nucleic acid molecules produced can be used in hybridisation studies of nucleic acid and nucleic acid sequencing. A wide variety of labels have been used in these techniques including radioactive isotopes, eg $^3H$, $^{14}C$, $^{32}P$, $^{33}P$ and $^{35}S$, hapten, biotin, mass tags or fluorescence.

There has been increasing interest in the use of modified base and nucleotide analogues in the labelling of nucleic acids. Some of these analogues are base specific and may be incorporated into nucleic acids in the place of a single natural base i.e. A, T, G or C. Other analogues have the potential to base pair with more than one natural base and hence be incorporated in the place of more than one natural base.

WO 97/28177 discloses nucleoside analogues containing the structure

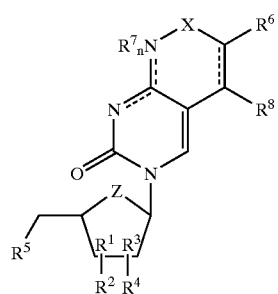

Wherein X is O, S, Se, SO, CO or $NR^7$
$R^1$, $R^2$, $R^3$ and $R^4$ are the same or different and each is H, OH, F, $NH_2$, $N_3$, O-hydorcarbyl or a reporter group,
$R^5$ is OH or mono-, di-, or tri-phosphate or thiophosphate or corresponding boranophosphate,
or one of $R^2$ and $R^5$ is a phosphoramidite,
Z is O, S, Se, SO, $NR^9$ or $CH_2$
and $R^6$, $R^7$, $R^8$, $R^9$ are the same or different and each is H, alkyl, aryl or a reporter group.
WO 99/06422 discloses base analogues of the structure

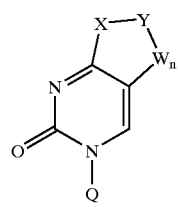

where X=O or NH or S
Y=N or $CHR^6$ or $CR^6$
W=N or $NR^6$ or $CHR^6$ or $CR^6$
n=1 or 2
each $R^6$ is independently H or O or alkyl or alkenyl or alkoxy or aryl or a reporter moiety, where necessary (i.e. when Y and/or W is N or $CR^6$) a double bond is present between Y and W or W and W,
Q is a sugar or sugar analogue

SUMMARY OF PRESENT INVENTION

The present invention describes novel compounds of the formula

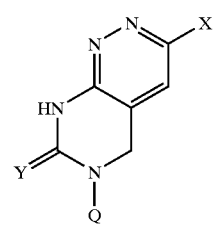

formula (I)

Wherein Q is H or a sugar or a sugar analogue or a nucleic acid backbone or backbone analogue, Y=O, S, $NR^{10}$, where $R^{10}$ is H, alkyl alkenyl, alkynyl, X is H, alkyl, alkenyl, alkynyl, aryl, heteroaryl or a combination thereof or, preferably, a reporter group.

DETAILED DESCRIPTION OF INVENTION

In a first aspect, the present invention provides novel compounds of the formula (I), Wherein Q is H or a sugar or a sugar analogue or a nucleic acid backbone or backbone analogue, Y=O, S, $NR^{10}$, where $R^{10}$ is H, alkyl alkenyl, alkynyl, X is H, alkyl, alkenyl, alkynyl, aryl, heteroaryl or a combination thereof or preferably a reporter group. The reporter group may be joined to the heterocycle via a suitable linker arm, which can be similar to the options already defined for X or may be larger. In this aspect, suitably X can comprise a chain of up to 30 atoms, more preferably up to 12 atoms. The reporter may contain more than 12 atoms. X may also contain a charged group, which imparts a net positive or negative charge to the nucleotide base.

Suitably, Q may be H or a group selected from

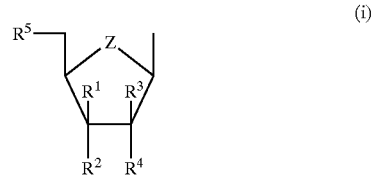

(i)

Where Z is O, S, Se, SO, $NR^9$ or $CH_2$ where $R^9$ is H, alkyl, alkenyl, alkynyl or a reporter, $R^1$, $R^2$, $R^3$ and $R^4$ are the same or different and each is H, OH, F, $NH_2$, $N_3$, O-hydrocarbyl, $NHR^{11}$ where $R^{11}$ is alkyl, alkenyl, alkynyl, or a reporter group. Suitably, the hydrocarbyl group has up to 6 carbon atoms. $R^{11}$ and $R^9$ may comprise a chain of up to 30 atoms, preferably up to 12 atoms.

$R^5$ is OH, SH or $NH_2$ or mono-, di or tri-phosphate or-thiophosphate, or corresponding boranophosphate, or one of $R^2$, $R^4$, and $R^5$ is a phosphoramidite or other group for incorporation in a polynucleotide chain, or a reporter group; or Q may be of one of the following modified sugar structures:

Acyclic sugars having structures (ii) or (iii)

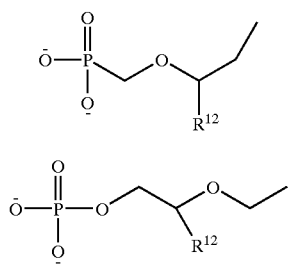

wherein $R^{12}$ is C1–C4 alkyl, hydroxyC1–C4alkyl, or H, preferably methyl, hydroxymethyl or H, or sugars having structures (iv) to (vi)

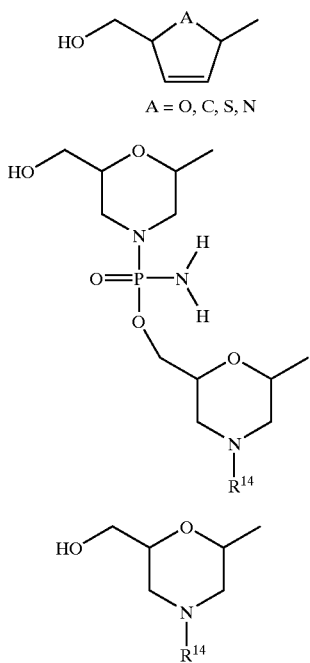

$R^{14}$=C1–C6 alkyl, hydroxy C1–C6 alkyl, C1–C6 alkylamine, C1–C6 carboxyalkyl or preferably a reporter moiety.

(vii) or Q is a nucleic acid backbone consisting of sugar-phosphate repeats or modified sugar phosphate repeats (e.g. LNA) (Koshkin et al, 1998, Tetrahedron 54, 3607–30) or a backbone analogue such as peptide or polyamide nucleic acid (PNA) (Nielsen et al, 1991, Science 254, 1497–1500) or a polycationic ribonucleic acid guanidine (RNG), Bruice et al, 1995 PNAS 92 6097, or pentopyranosyl oligonucleotides (HNA), Eschenmosser A., 1999, Science, 284 2118–2124.

In one preferred embodiment, when Q is H, these compounds are base analogues. In a second preferred embodiment, Q is a sugar or sugar analogue or a modified sugar, e.g. a group having a structure according to (i) to (vi) and the compounds are nucleotide analogues or nucleoside analogues. When Q is a nucleic acid backbone or a backbone analogue, (vii), these compounds are herein after called nucleic acids or polynucleotides.

When Q is a group of structure (i) $R^1$, $R^2$, $R^3$ and $R^4$ may each be H, OH, F, $NH_2$, $N_3$, O-alkyl or a reporter moiety. Thus ribonucleosides and deoxyribonucleosides and dideoxyribonucleosides are envisaged together with other nucleoside analogues. These sugar substituents may contain a reporter group in addition to any that might be present on the base Preferably, $R^1$=H, $R^2$=H, OH, F, $N_3$, $NH_2$, $NH(CH_2)n$ $R^{13}$ or O—$(CH_2)_nNH_2$ where n is 0–12, $R^4$=H, OH, $N_3$, $NH_2$, F, $OR^3$, $R^3$=H, OH or $OR^{13}$ where $R^{13}$ is alkyl, alkenyl, alkynyl or a reporter. More preferably at least one of $R^1$ and $R^2$ and at least one of $R^3$ and $R^4$ is H.

$R^5$ is OH, SH, $NH_2$ or mono, di- or tri-phosphate or thiotriphosphate or corresponding boranophosphate. When $R^5$ is triphosphate, such triphosphate nucleotides may be incorporated into a polynucleotide chain by using a suitable template- primer together with a DNA polymerase or reverse transcriptase and appropriate dNTPs and ddNTPs when necessary. NTPs can be used with suitable RNA polymerases. The compounds of the present invention may be incorporated into a PCR product using standard techniques or used in the production of cDNA from a suitable RNA template, primer dNTP mix and reverse transcriptase. Oligonucleotide and polynucleotide chains may also be extended by nucleotide analogues of the present invention by the use of terminal transferase.

Alternatively, one of $R^2$, $R^4$, and $R^5$ may be a phosphoramidite or H-phosphonate or methylphosphonate or phosphorothioate or amide, or an appropriate linkage to a solid surface e.g. hemisuccinate controlled pore glass, or other group for incorporation, generally by chemical means, in a polynucleotide chain. The use of phosphoramidites and related derivatives in synthesising oligonucleotides is well known and described in the literature.

In another preferred embodiment, the nucleoside analogue or nucleotide analogue which contains a base analogue as defined is labelled with at least one reporter group. Suitable reporter moieties may be selected from various types of reporter. The reporter group may be a radioisotope by means of which the nucleoside analogue is rendered easily detectable, for example $^{32}P$ or $^{33}P$ or $^{35}S$ incorporated in a phosphate or thiophosphate or phosphoramidite or H-phosphonate group, or alternatively $^3H$ or $^{14}C$ or an iodine isotope. It may be an isotope detectable by mass spectrometry or NMR. It may be a signal group or moiety e.g. an enzyme, hapten, fluorophore, chromophore, chemiluminescent group, Raman label or electrochemical label. Particularly preferred reporters are fluorescent dyes such as fluorescein, rhodamine, bodipy and cyanines.

The reporter group may comprise a signal group or moiety and a linker group joining it to the remainder of the molecule. The linker group may be a chain of up to 30 carbon, nitrogen, oxygen and sulphur atoms, rigid or flexible, saturated or unsaturated. Such linkers are well known to those skilled in the art. The linker group may have a terminal or other group eg $NH_2$, OH, COOH, SH, maleimido, haloacetyl or other group by which a signal moiety may be attached before or after incorporation of the nucleoside analogue into a nucleic acid chain. It is also possible to link the molecules of the present invention to a solid surface through a suitable linker group as described above.

It is also possible that molecules of the present invention may act as reporters themselves. Antibodies may be raised to the whole molecule or part of the molecule e.g. ring structure or modified sugar. The antibodies can carry labels themselves or be detected by second antibodies by methods well known in the art. These methods often use enzyme detection or fluorescence.

The nucleoside analogues of this invention can be used in any of the existing applications which use native nucleic acid probes labelled with haptens, fluorophores or other reporter groups. These include Southern blots, dot blots and in polyacrylamide or agarose gel based methods or solution hybridisation assays and other assays in microtitre plates or tubes or assays of oligonucleotides or nucleic acids on arrays on solid supports. The probes may be detected with antibodies targeted either against haptens which are attached to the analogue or against the analogues themselves. The antibody can be labelled with an enzyme or fluorophore. Fluorescent detection may also be used if the base analogue is itself fluorescent or if there is a fluorescent group attached to the analogue.

The use of the different mass of the nucleoside analogue may also be used in detection as well as by the addition of a specific mass tag identifier to it. Methods for the analysis and detection of oligonucleotides, nucleic acid fragments and primer extension products have been reported (U.S. Pat. No. 5,288,644 and WO 94/16101). These methods are usually based on MALDI ToF mass spectrometry. They measure the total mass of an oligonucleotide and from this the sequence of the oligonucleotide may be ascertained. In some cases the mass of the oligonucleotide or fragment may not be unique for a specific sequence. This will occur when the ratio of the natural bases, ACGT is similar in different sequences. For example the simple 4 mer oligonucleotide will have the same mass as 24 other possible 4 mers e.g. CAGT, CATG, CGTA etc.

With longer nucleic acid fragments, it may be difficult to resolve differences in mass between two fragments due to a lack of resolution in the mass spectrum at higher molecular weights. Incorporation of base modified analogues according to the present invention can be used to help identify the specific oligonucleotide or nucleic acid fragment, as their masses are different from those of the natural bases. For example, the two sequences ACGT and CAGT can be identified in the presence of one another by mass spectrometry if one of the natural nucleotides in one of the sequences is replaced with one of the analogues of the present invention. For example, in the oligonucleotide CAGT, the T can be replaced with an analogue of the present invention with little effect on a specific application e.g. hybridisation or enzymatic incorporation. Yet the two sequences can be readily identified by mass spectrometry because of the change in mass due to the introduction of the analogue.

The modification can be made to the bases and also to the sugars or inter nucleotide linkage. For example thio sugars or phosphothioate linkages will also result in distinctive mass changes. A large variety of changes to the base, sugar or linker can yield a number of molecules of different masses which will be useful to define a specific sequence accurately by its mass, especially in multiplex nucleic acid hybridisation or sequencing applications.

RNA is an extremely versatile biological molecule. Experimental studies by several laboratories have shown that in vitro selection techniques can be employed to isolate short RNA molecules from RNA libraries that bind with high affinity and specificity to proteins, not normally associated with RNA binding, including a few antibodies, (Gold, Allen, Binkley, et al, 1993, 497–510 in The RNA World, Cold Spring Harbor Press, Cold Spring Harbor N.Y., Gold, Polisky, Uhlenbeck, and Yarus, 1995, Annu. Rev. Biochem. 64: 763–795, Tuerk and Gold, 1990, Science 249:505–510, Joyce, 1989, Gene 82:83–87, Szostak, 1992, Trends Biochem. Sci 17:89–93, Tsai, Kenan and Keene, 1992, PNAS 89:8864–8868, Tsai, Kenan and Keene, 1992, PNAS 89:8864–8868, Doudna, Cech and Sullenger, 1995, PNAS 92:2355–2359). Some of these RNA molecules have been proposed as drug candidates for the treatment of diseases like myasthenia gravis and several other auto-immune diseases.

The basic principle involves adding an RNA library to the protein or molecule of interest. Washing to remove unbound RNA. Then specifically eluting the RNA bound to the protein or other molecule of interest. This eluted RNA is then reverse transcribed and amplified by PCR. The DNA is then transcribed using modified nucleotides (either 2' modifications to give nuclease resistance e.g. 2' F, 2' $NH_2$, 2' $OCH_3$ and/or C5 modified pyrimidines and/or C8 modified purines). Those molecules that are found to bind the protein or other molecule of interest are cloned and sequenced to look for common ("consensus") sequences. This sequence is optimised to produce a short oligonucleotide which shows improved specific binding which may then be used as a therapeutic.

The base analogues described here, when converted to the ribonucleoside triphosphate or ribonucleoside phosphoramidite, will significantly increase the molecular diversity available for this selection process. This may lead to oligonucleotides with increased binding affinity to the target that is not available using the current building blocks.

The analogues of the present invention may have properties which are different to those of the native bases and have other important applications. They may find use in the antisense field. They may also be useful in the therapeutic field as antiviral (anti-HIV and anti-HBV etc) (WO 98/49177) and anticancer agents. Many nucleoside and nucleotide analogues have been developed as antiviral agents. They often act by inhibition of DNA polymerase and/or reverse transcriptase activity by a number of means. A number of nucleoside analogues, such as AZT, ddC, ddI, D4T, and 3TC are being used alone or in combination of other nucleoside or non-nucleoside analogues as anti-HIV agents. The analogues of the present invention may also have antiviral activities alone or in combination with other compounds. Since combination drug therapy is being used more frequently to treat viral infections, having an increased number of compounds available by including compounds of the present invention could enhance the possibility of successful treatments.

Particularly preferred compounds of the invention are compounds of formula (II)

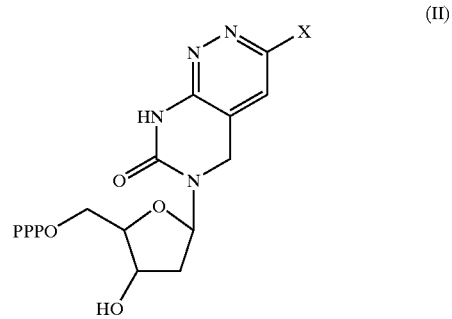

Wherein X is as herein before defined.

The invention will now be further described with reference to the following non-limiting examples.

SYNTHETIC EXAMPLE 1

Synthesis of 6-(β-D-2-Deoxyribofuranosyl)-5-hydro-3-methyl-8H-pyrimido[4,5-c][1,2]pyridazin-7-one-5'-triphosphate (5).

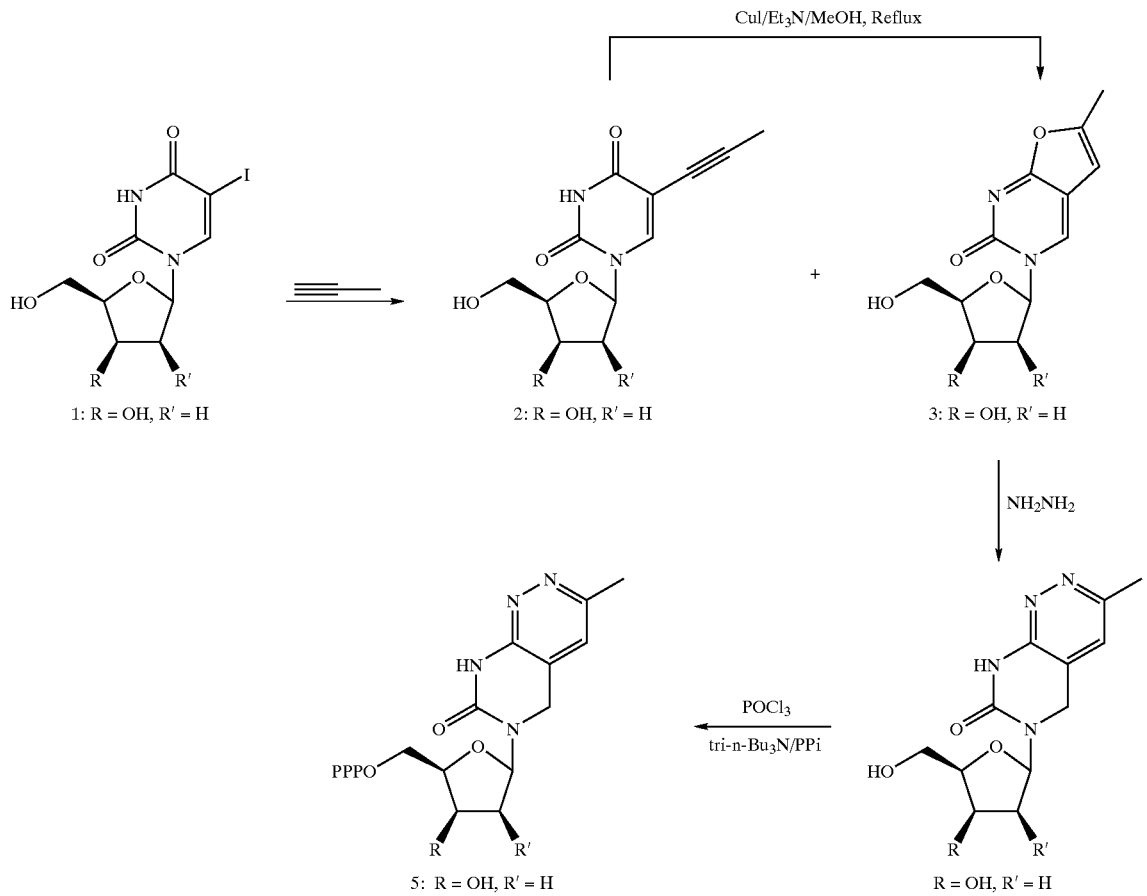

(a) 3-(β-D-2-Deoxyribofuranosyl)-6-methyl-furo[2,3-d]pyrimidin-2-one (3).

To a 100-ml glass pressure reaction vessel under argon was added 7.1 g (20 mmol) of 5-iodo-(β-D-2-deoxyribofuranosyl)uridine, 2.32 g (2 mmol) of tetrakis(triphenylphosphine)palladium(0), and 0.76 g (4 mmol) of copper(I)iodide. Anhydrous DMF (50 ml) and triethylamine (4.2 ml, 30 mmol) were then injected into the reaction vessel. Into the stirred and cooled (0° C.) reaction mixture, propyne gas was bubbled for ten minutes. Upon sealing the pressure vessel, the temperature of the reactants was increased to 55–60° C. via an oil bath. The reaction was allowed to stir under these conditions for 18 hours. On cooling, no starting material was detected by TLC analysis. Methanol (25 ml), Chelex 100 resin (5 g, 200–400 mesh, sodium form) and AG 1-X8 resin (5 g, 20–50 mesh, bicarbonate form) were added to the reaction mixture and stirred gently for one hour. After filtration, the solution was evaporated to an oil under high vacuum. The residue was purified by silica gel column chromatography (chloroform/MeOH 100% to 10:1) yielding 5-propynyl-(β-D-2-deoxyribofuranosyl)uridine 2 (rf: 0.4) as a tan foam in 45% yield, and 3-(β-D-2-deoxyribofuranosyl)-6-methyl-furo[2,3-d]pyrimidin-2-one 3 (rf: 0.2) as a yellow solid in 50% yield. 5-Propynyl-(β-D-2-deoxyribofuranosyl)uridine was converted to 3-(β-D-2-deoxyribofuranosyl)-6-methyl-furo[2,3-d]pyrimidin-2-one by refluxing in methanol/triethylamine (7:3) containing 5% copper(I)iodide for 2 hours. After column chromatography a 61% yield was obtained. $^1$H NMR (DMSO-d$_6$): 2.06 (m, 1H, 2'), 2.33 (s, 3H, Me), 3.38 (m, 1H, 2'), 3.65 (m, 2H, 5'), 3.91 (q, 1H, 4'), 4.24 (m, 1H, 3'), 5.09 (t,1H, OH-5'), 5.26 (d,1H, OH-3'), 6.18 (t, 1H, 1'), 6.41 (s, 1H, H-5), 8.66 (s, 1H, H-4). $^{13}$C NMR (DMSO-d$_6$): 29.8 (Me), 40.3 (2'), 60.8 (5'), 69.9 (3'), 85.3 (1'), 88.1 (4'), 88.8 (C-5), 98.3 (C-4a), 144.8 (C-4), 147.8 (C-6), 150.1 (C-2), 162.1 (C-7a).

b) (6-(β-D-2-Deoxyribofuranosyl)-5-hydro-3-methyl-8H-pyrimido[4,5-c][1,2]pyridazin-7-one (4).

To 500 mg (1.35 mmol) of 3-(β-D-2-deoxyribofuranosyl)-6-methyl-furo[2,3-d]pyrimidin-2-one (3) in a 25 ml round bottom flask was added 6 ml of anhydrous hydrazine. The reaction mixture was allowed to stir at room temperature for 2 hours. The excess hydrazine was then removed by evaporation under high vacuum. The residue was purified by silica gel column chromatography (chloroform/MeOH 10:1) to yield an off white crystalline product in 85% yield. X-ray quality crystals were obtained from methanol. $^1$H NMR (DMSO-d$_6$): 1.80 (m, 1H, 2'), 2.14 (m, 1H, 2'), 2.49 (s, 3H, Me), 3.49 (m, 2H, 5'), 3.62 (q, 1H, 4'), 4.16 (m, 1H, 3'), 4.40 (s, 2H, H-5), 4.79 (t,1H, OH-5'), 5.13 (d, 1H, OH-3'), 6.24 (t, 1H, 1'), 7.34 (s, 1H, H-4), 10.29 (bs, 1H, NH-8). $^{13}$C NMR (DMSO-d$_6$): 21.1 (Me), 35.1 (2'), 47.8 (C-5), 61.8 (5'), 70.6 (3'), 83.1 (1'), 86.0 (4'), 120.8 (C-4a), 124.8 (C-4), 151.8 (C-7), 153.2 (C-3), 155.2 (C-8a).

c) 6-(β-D-2-Deoxyribofuranosyl)-5-hydro-3-methyl-8H-pyrimido[4,5-c][1,2]pyridazin-7-one-5'-triphosphate (5).

To 140 mg (0.5 mmol) of dried 6-(β-D-2-Deoxyribofuranosyl)-5-hydro-3-methyl-8H-pyrimido[4,5- c][1,2]pyridazin-7-one (4) in a 50 ml round bottom flask under argon was added 5 ml of trimethylphosphate. The homogenous solution was cooled (ice bath) and 70 µl (0.75 mmol, 1.5 eq.) of phosphorus oxychloride (redistilled) was added. The reaction was stirred with cooling for one hour. TLC analysis indicated the reaction to be about 70% complete. Therefore, 25 µl (0.27 mmol, 0.51 eq.) of additional phosphorus oxychloride was added and the reaction allowed to stir for an additional hour. Both 1 M tributylammonium pyrophosphate in anhydrous DMF (2.5 ml, 2.5 mmol, 5 eq.) and n-tributylamine (0.6 ml, 2.5 mmol, 5 eq.) were simultaneously added to the cooled solution. After 30 minutes cooled 1 M triethylammonium bicarbonate buffer (TEAB, pH=7.0) was added to the reaction mixture until the solution became neutral. The buffer was then added to a final volume of 40 ml and the mixture was stirred overnight at room temperature. The reaction mixture was evaporated under high vacuum to a viscous solution, diluted with water and filtered. The filtrate containing crude triphosphate was then applied to a 50×300 mm DeltaPak (15µ, 100A) C18HPLC column which was eluted using a linear gradient over 25 min. with 0.1 M TEAB (pH=7.0) to 0.1 M TEAB in 25% acetonitrile at a flow rate of 130 ml per minute. A peak containing the product 5 was collected at 10.5 minutes. After evaporation, the triphosphate obtained was repurified on a 21×250 mm Synchropak A×100HPLC column using a linear gradient for 30 minutes at 15 ml per minute of 0.1 M TEAB in 40% CH$_3$CN to 1 M TEAB in 40% CH$_3$CN. $^{31}$P NMR (D$_2$O): −9.26 (d); −10.20 (d); −22.43 (t). HPLC (Δ PAK C 18, 3.9 by 30 cm, 0.1 M TEAB (pH=7.0) to 0.1 M TEAB in 25% CH$_3$CN in 30 minutes at 1 ml per minute) 12.7 minutes. UV λmax 237 nm and 292 nm.

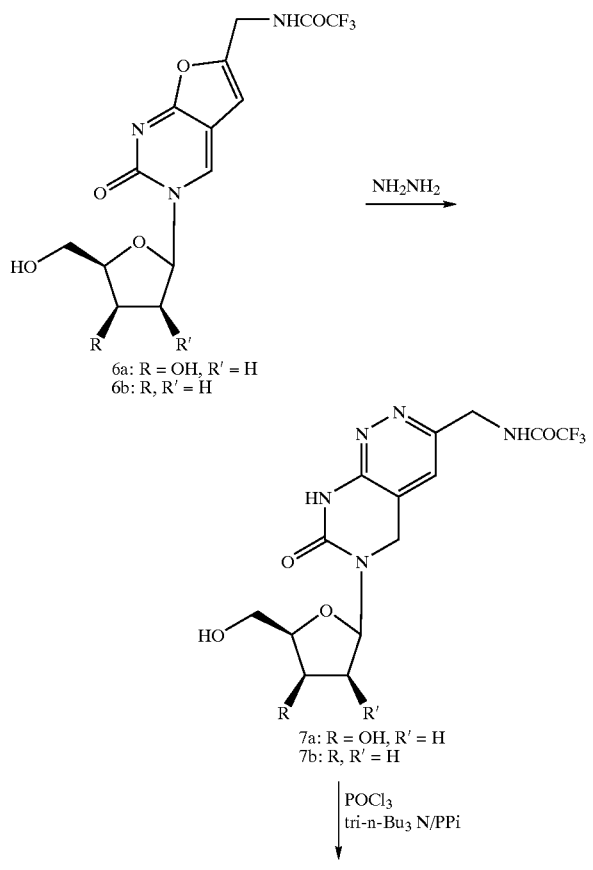

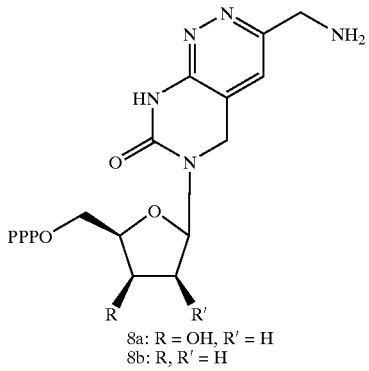

8a: R = OH, R' = H
8b: R, R' = H

SYNTHETIC EXAMPLE 2

Synthesis of 6-(β-D-2-Deoxyribofuranosyl)-5-hydro-3-aminomethyl-8H-pyrimido [4,5-c][1,2]pyridazin-7-one-5'-triphosphate (8a).

a) 3-(β-D-2-Deoxyribofuranosyl)-6-trifluoroacetamidomethyl-furo [2,3-]pyrimidin-2-one (6a).

Triethylamine (3.04 g, 4.2 mL, 30 mmol, 1.5 eq) was added to a stirred solution of 5-iodo-2'-deoxyuridine (7.1 g, 20 mmol, 1 eq), Pd[P(C$_6$H$_5$)$_3$]$_4$ (1.16 g, 1 mmol, 0.05 eq), CuI (0.38 g, 2 mmol, 0.1 eq) and 2,2,2-trifluoro-N-propargyl acetamide (4.53 g, 30 mol, 1.5 eq) in dry DMF (75 mL) and the resulting mixture was then stirred for two days at 55° C. under inert atmosphere. To the reaction mixture was then added the bicarbonate form of AG1 X8 resin to remove triethylammonum hydroiodide, CHELEX resin to remove metal cations and activated charcoal to remove colour. After filtration on celite a slightly yellow solution was produced. Solvent removal under vacuum and silica gel chromatography yielded 4.2 g (56%) of 6a. UV (MeOH) λmax 324 nm; $^1$H NMR (d$_6$-DMSO) δ (ppm) 10.07 (s, 1H, exchangeable, H—NH—COCF3), 8.78 (s, 1H, H-6), 6.63 (s, 1H, H—CH=C(O)CH$_2$), 6.18 (t, J=6.55 Hz, H-1'), 5.00–5.3 (bm, 2H, exchangeable, 2×OH), 4.48 (m, 2H, H—CH$_2$—NH), 4.23 (m, 1H, H-4'), 3.95 (m, 1H, H-3'), 3.63 (m, 2H, H-5'), 2.40 (m, 1H, H-2'b), 2.07 (m, 1H, H-2'a)

b) 3-(β-D-2,3-dideoxyribofuranosyl)-6-trifluoroacetamidomethyl-furo[2,3-d]pyrimidin-2-one (6b).

The title compound was prepared following the procedure described for 3-(β-D-2-deoxyribofuranosyl)-6-methyl-furo [2,3-d]pyrimidin-2-one. $^1$H NMR (CD$_3$OD): 1.94 (m, 2H, 3'), 2.01 (s, 3H, Me), 2.18 (m, 1H, 2'), 2.57 (m, 1H, 2'), 3.75–4.06 (ddd, 2H, 5'), 4.27 (m, 1H, 4'), 4.52 (s, 2H, CH$_2$NH), 6.11 (dd, 1H, 1'), 6.65 (s, 1H, H-5), 9.13 (s, 1H, H-4).

c) 6-(β-D-2-Deoxyribofuranosyl)-5-hydro-3-trifluoroacetamidomethyl-8H-pyrimido[4,5-c][1,2]pyridazin-7-one (7a).

To 754 mg (2 mmol) of 3-(β-D-2-deoxyribofuranosyl)-6-trifluoroacetamidomethyl-furo[2,3-d]pyrimidin-2-one (6a) in a 25 ml round bottom flask was added 5 ml of anhydrous hydrazine. The reaction mixture was allowed to stir at room temperature for 3 hours. The excess hydrazine was then removed by evaporation under high vacuum. To the residue 20 ml of methanol, 0.5 ml of triethylamine followed by 5 ml ethyl trifluoroacetate was added. The reaction mixture becomes homogenous with stirring after about one hour. After overnight stirring at room temperature, the reaction mixture was evaporated and the residue obtained was purified by silica gel column chromatography (EtOAc/MeOH 20:1). A pale yellow crystalline compound was collected in 86% yield. ¹H NMR (DMSO-d₆): 1.79 (m, 1H, 2'), 2.15 (m, 1H, 2'), 3.49 (m, 2H, 5'), 3.61 (q, 1H, 4'), 4.15 (m, 1H, 3'), 4.46 (d, 2H, H-5), 4.57 (d, 2H, CH₂NH), 4.81 (t, 1H, OH-5'), 5.14 (d,1H, OH-3'), 6.24 (t, 1H, 1'), 7.43 (s, 1H, H-4), 10.1 (t, 1H, NH-TFA), 10.51 (s, 1H, NH-8).). ¹³C NMR (DMSO-d₆): 35.1 (CH₂NH), 39.0 (2'), 42.8 (C-5), 61.7 (5'), 70.5 (3'), 83.0 (1'), 85.9 (4'), 117.9 (CF₃), 121.2 (C-4), 123.4 (C-4a), 152.7, 152.8 (C-3, C-7), 154.2 (C-8a), 156.7 (q, COCF₃).

d) 6-(β-D-2-Deoxyribofuranosyl)-5-hydro-3-aminomethyl-8H-pyrimido [4,5-c][1,2]pyridazin-7-one-5'-triphosphate (8a).

The phosphorylation of 200 mg (0.51 mmol) of dried 6-(β-D-2-Deoxyribofuranosyl)-5-hydro-3-trifluoroacetamidomethyl-8H-pyrimido[4,5-c][1,2]pyridazin-7-one (7a) was carried out the same way as reported above for compound 5. The crude mixture was applied to a 50×300 mm DeltaPak (15μ, 100A) C18HPLC column which was eluted using a linear gradient over 25 min. with 0.1 M TEAB (pH=7.0) to 0.1 M TEAB in 25% acetonitrile at a flow rate of 130 ml per minute. A peak containing the product was collected at 15 minutes. After evaporation, the triphosphate obtained was repurified on a 21×250 mm Synchropak A×100HPLC column using a linear gradient for 30 minutes at 15 ml per minute of 0.1 M TEAB in 40% CH₃CN to 1 M TEAB in 40% CH₃CN. The triphosphate was treated with conc. NH₄OH for 30 minutes without change as observed by analytical HPLC, verifying that the trifluoroacetyl-protecting group had been removed prior to this step. ³¹P NMR (D₂O): −9.65 (d), −10.86 (d), −22.54 (t). HPLC (Δ PAK C 18, 3.9×30 cm, 0.1 M TEAB (pH=7.0) to 0.1 M TEAB in 25% CH₃CN in 30 minutes at 1 ml per minute) 12.2 minutes. UV λmax 241 nm and 293 nm.

e) 6-(β-D-2,3-Dideoxyribofuranosyl)-5-hydro-3-trifluoroacetamidomethyl-8H-pyrimido[4,5-c][1,2]pyridazin-7-one (7b).

The synthesis was carried out as reported above for compound 7a. A tan foam was collected in 65% yield. ¹H NMR (CD₃OD): 1.84–2.23 (m, 4H, 2',3'), 2.01 (s, 3H, Me), 3.58–3.78 (m, 2H, 5'), 3.99 (m, 1H, 4'), 4.50–4.71 (dd, 2H, H-5), 4.66 (s, 2H, CH₂NH), 6.22 (dd, 1H, 1'), 7.48 (s, 1H, H-4).

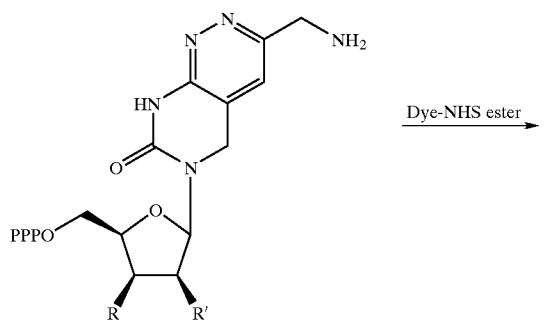

8a: R = OH, R' = H
8b: R, R' = H

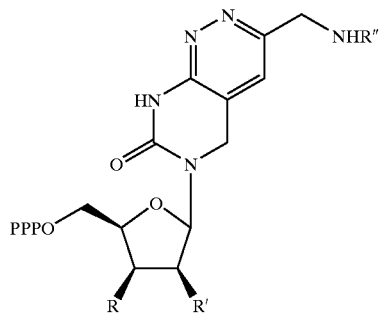

9a: R = OH, R' = H, R'' = Cy3,
9a': R = OH, R' = H, R'' = Cy5.5
9a'': R = OH, R' = H, R'' = (5,6)-Carboxy-x-fluorescein
9a''': R = OH, R' = H, R'' = Cy5
9b: R, R' = H

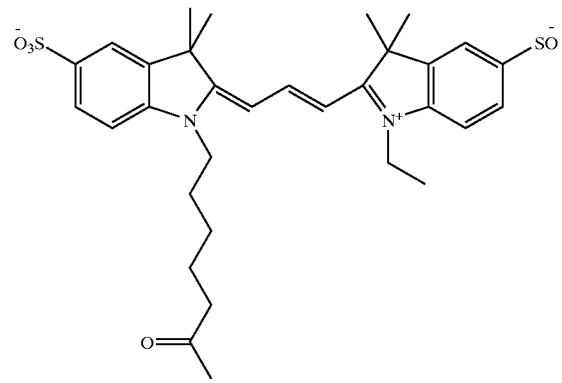

Cy3

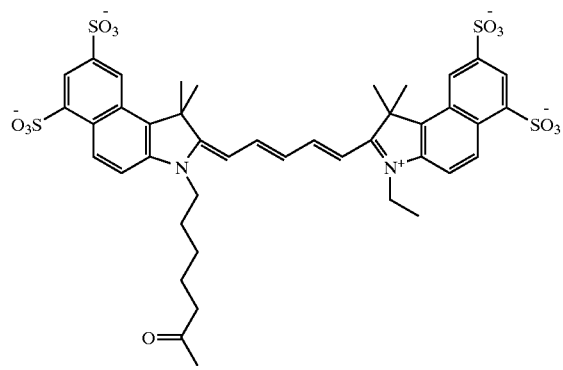

Cy5.5

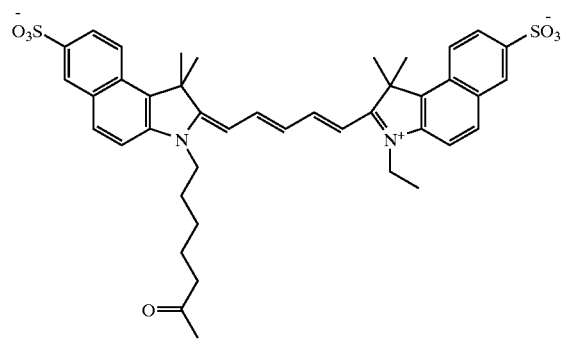

Cy5

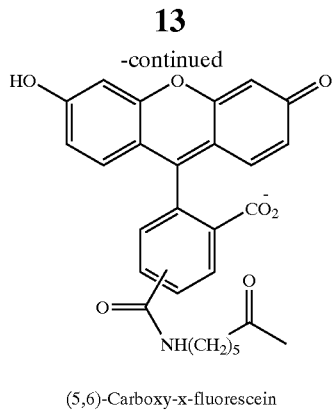

(5,6)-Carboxy-x-fluorescein

EXAMPLE 3

Synthesis of 6-(β-D-1,2-Dideoxyribofuranosyl)-5-hydro-3-aminomethyl-8H-pyrimido [4,5-c][1,2]pyridazin-7-one-5'-triphosphate (8b).

The synthesis (on 0.73 mmol scale) and purification/isolation of 8b was carried out as described for compound 5.

Synthesis of 6-(β-D-2-Deoxyribofuranosyl)-5-hydro-3-Cy3-amidomethyl-8H-pyrimido [4,5-c][1,2]pyridazin-7-one-5'-triphosphate (9a).

6.0 μmol (690 μL aqueous solution) of 8a was diluted with 310 μL of $Na_2CO_3$—$NaHCO_3$ buffer (pH=9.4) and added to a stirred DMF (1.0 mL) solution of Cy3-NHS ester (7.2 μmol, 1.2 eq.). After 2 h of stirring at room temperature, the Cy3 dye-nucleotide conjugate (9a) was isolated (35%) by purifying on a Q-Sepharose HPLC column (10×16 mm), using a linear gradient of buffer A (40% $CH_3CN$ in 0.1 M TEAB) to buffer B (40% $CH_3CN$ in 1.0 M TEAB) in 60 min at 5 mL/min. TOF MS ES-m/z, cone 100 v, $CH_3CN/H_2O$: 1144 (MH-3).

Synthesis of 6-(β-D-2-Deoxyribofuranosyl)-5-hydro-3-Cy5.5-amidomethyl-8H-pyrimido[4,5-c][1,2]pyridazin-7-one-5'-triphosphate (9a').

The Cy5.5 fluorescent dye nucleotide-conjugate (9a') was synthesized and isolated (33% yield) on a similar scale by reacting 8a with Cy5.5 NHS ester as described for 9a.

Synthesis of 6-(β-D-2-Deoxyribofuranosyl)-5-hydro-3-fluorescein(5,6) hexanamido-amidomethyl-8H-pyrimido [4,5-c][1,2]pyridazin-7-one-5'-triphosphate (9a").

8.0 μmol (aq.solution) of 8a was diluted with 1.0 mL of $Na_2CO_3$—$NaHCO_3$ buffer (pH=9.0) and to the stirred solution was added anhy. DMSO solution of (5,6)-carboxy-x-NHS ester (17.0 μmol, 2.1 eq.). After 2 h, the dye labelled nucleotide was purified on a Q-Sepharose column as described for 9a to give 9a". TOF MS ES-m/z, cone 100 v, $CH_3CN/H_2O$: 1003 (MH-3).

EXAMPLE 4

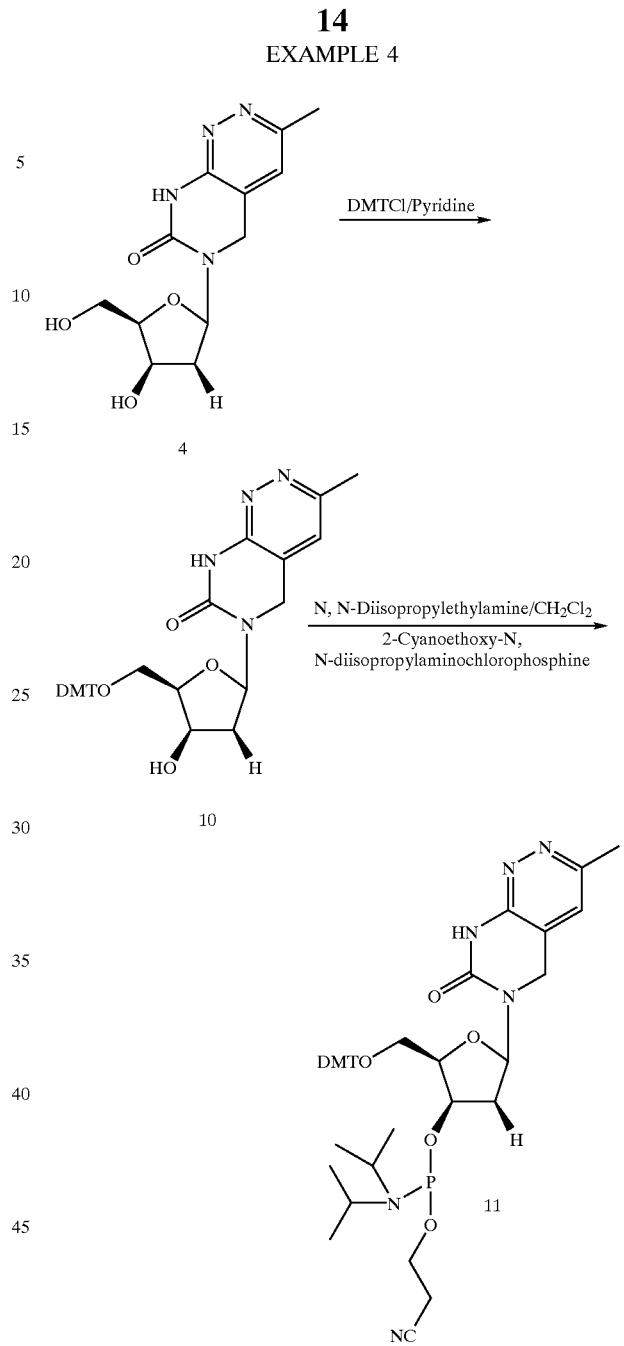

Synthesis of 6-(5-Dimethoxytrityl-β-D-2-deoxyribofuranosyl)-5-hydro-3-methyl-8H-pyrimido[4,5-c][1,2]pyridazin-7-one (10).

1.16 g (4.1 mmol) of the 4 was co-evaporated with anhydrous pyridine and re-dissolved in 30 mL of anhydrous pyridine. 4.15 g (12.24 mmol, 3 eq.) of DMT-Cl was added to the stirred solution of 4, at room temperature under Ar atmosphere. After 3.5 h, the reaction mixture was evaporated under reduced pressure and residue dissolved in $CHCl_3$. The organic layer was washed with saturated $NaHCO_3$ solution, dried with anhydrous $Na_2SO_4$ and evaporated under reduced pressure. The residue obtained was purified on a silica gel column eluting with $CHCl_3$ followed by 5% MeOH in $CHCl_3$ to afford 10 (2.35 g, 99%). TOF MS ES-m/z, cone 100 v, $CH_3CN$/0.1 M TEAB: 581.24 (MH-1).

Synthesis of 6-(5-O-Dimethoxytrityl-3-O-(2-cyanoethyl N,N-diisopropylphosphoramidite)-β-D-2-deoxyribofuranosyl)-5-hydro-3-methyl-8H-pyrimido[4,5-c][1,2]pyridazin-7-one (11)

583 mg (1.0 mmol) of compound 10 was co-evaporated with anhydrous pyridine followed by toluene and dissolved in anhydrous dichloromethane (5 mL). To the stirred solution under a slow stream of Ar, at room temperature, 0.7 mL (4.0 mmol, 4.0 eq.) of N,N-diisopropylethylamine was added followed by dropwise addition of 2-cyanoethoxy N,N-diisopropylaminochlorophosphine (0.28 mL, 1.25 mmol, s). After 30 min, TLC in 10% MeOH—$CHCl_3$ indicated completion of the reaction. The reaction mixture was diluted with $CH_2Cl_2$, washed with 10% $Na_2CO_3$, and the organic layer after drying (anhy. $Na_2SO_4$) was evaporated under reduced pressure. The residue obtained was purified on a silica gel column (4×13 cm) eluting with $CH_2Cl_2$:EtOAc:$Et_3N$ (2.9:7:0.1) to give 11 (570 mg, 73%).
$^{31}$P NMR ($CDCl_3$): δ149.66.

or 40 μM (test compound 5c) or a mixture of 4 μM dNTPαS and 40 μM (test compound). One unit EFK and 20 mU inorganic pyrophosphatase were used per reaction. Primer alone, primer plus template plus enzyme controls were also carried out. The reactions were incubated at 37° C. for 3 minutes. Reactions were then stopped by the addition of formamide/EDTA stop solution. Reaction products were separated on a 20% polyacrylamide 7M urea gel and the product fragments sized by comparison with the labelled primer and the products of extensions in the presence of 4 μM dNTPαS after exposure to Kodak Biomax autoradiography film.

This showed that the test compound was a substrate for EFK and that it was incorporated in place of dTTP. Other compounds of the invention containing groups such as fluorescein or cyanine may be incorporated by similar methods.

SEQUENCE LISTING

<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 1
tgcatgtgct ggaga                                                      15

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 2
acgtacacga cctctgaact agtc                                            24

EXAMPLE 5
Primer Extension Assays to Study the Incorporation of Triphosphate 5 by DNA Polymerases A primer extension assay was used to evaluate the triphosphate 5 as a substrate for exonuclease free Klenow fragment DNA polymerase I (EFK). The assay used a $^{33}$P 5' end labelled 15 mer primer hybridised to a 24 mer template. The sequences of the primer and template are:

```
                                        (SEQ ID NO. 1)
Primer    5'TGCATGTGCTGGAGA 3'

(SEQ ID NO. 2)
Template  3'ACGTACACGACCTCTGAACTAGTC 5'
```

One picomole $^{33}$P labelled primer was hybridised to 2 picomoles of template in ×2 Klenow buffer (100 mM Tris-HCl pH 7.5, 10 mM $MgCl_2$., 10 mM 2-mercaptoethanol) To this was added either 4 μM dNTPαS

What is claimed is:
1. A compound comprising

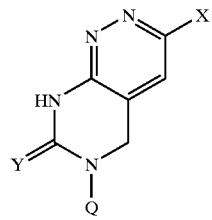

wherein:
Q is H or a sugar or a sugar analogue or a nucleic acid backbone or backbone analogue;
X is H, alkyl, alkenyl, alkynyl, aryl, hetero-aryl or a combination thereof or a reporter; and
Y=O, S, NR where R is H, alkyl, alkenyl, or alkynyl.

2. The compound as claimed in claim 1, which is a nucleoside or nucleoside analogue wherein Q has the structure

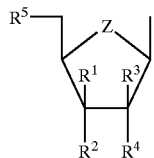

wherein:

Z is O, S, Se, SO, $NR^9$ or $CH_2$;

$R^9$ is H, alkyl, alkenyl, alkynyl or a reporter;

$R^1$, $R^2$, $R^3$ and $R^4$ are the same or different and each is H, OH, F, $NH_2$, $N_3$, O-hydrocarbyl, NHR or a reporter moiety;

R is alkyl, alkenyl or alkynyl; and $R^5$ is OH, SH or $NH_2$ or mono-, di or triphosphate or thiophosphate, or corresponding boranophosphate, or one of $R^2$, $R^4$, and $R^5$ is a phosphoramidite or other group for incorporation in a polynucleotide chain, or a reporter moiety.

3. The compound as claimed in claim 1, which is a nucleoside or nucleoside analogue wherein Q is selected from the group consisting of the following modified sugar structures:

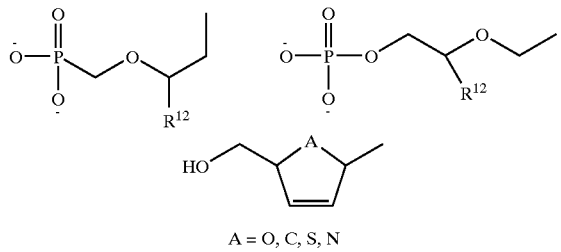

A = O, C, S, N wherein:

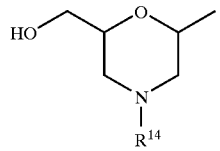

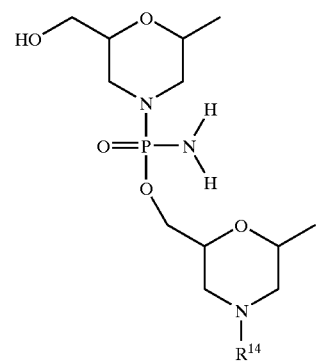

$R^{12}$ is C1–C4 alkyl; hydroxyC1–C4alkyl; or H; and wherein $R^{14}$ is C1–C6 alkyl, hydroxy C1–C6 alkyl, C1–C6 alkylamine, C1–C6 carboxyalkyl or a reporter moiety.

4. The compound as claimed in claim 1, which is a polynucleotide wherein Q is selected from the group consisting of nucleic acid backbones containing sugar-phosphate repeats or modified sugar-phosphate repeats (LNA), and backbone analogues such as peptide or polyamide nucleic acid (PNA).

5. The compound as claimed in claim 1, wherein a reporter moiety is present.

6. The compound as claimed in claim 5, wherein the reporter moiety is a signal moiety.

7. The compound as claimed in claim 5, wherein the reporter moiety is a reactive group or signal moiety or solid surface joined to the remainder of the molecule by a linker of at least 2 chain atoms.

8. The compound as claimed in claim 1, wherein X imparts net positive or negative charge to the nucleotide base.

9. The compound as claimed in claim 1, wherein $R^5$ is triphosphate.

10. The compound as claimed in claim 1, where one of $R^2$, $R^4$ and $R^5$ is selected from phosphoramidite and H-phosphonate.

11. A polynucleotide comprising at least one residue of a nucleotide analogue according to claim 1.

12. The polynucleotide as claimed in claim 11 which is DNA or RNA.

* * * * *